(12) United States Patent
Crippa et al.

(10) Patent No.: US 8,933,272 B2
(45) Date of Patent: Jan. 13, 2015

(54) PROCESS FOR THE PRODUCTION OF HEXAMETHLENEDIAMINE

(75) Inventors: Tommaso Crippa, Missaglia (IT); Stefano Alini, Cava Manara (IT); Luciano Guida, Mortara (IT); Alberto Corona, Vercelli (IT)

(73) Assignee: Radici Chimica S.p.A., Bergamo (IT)

( * ) Notice: Subject to any disclaimer, the term of this patent is extended or adjusted under 35 U.S.C. 154(b) by 0 days.

(21) Appl. No.: 14/110,823

(22) PCT Filed: Apr. 15, 2011

(86) PCT No.: PCT/EP2011/055996
§ 371 (c)(1),
(2), (4) Date: Oct. 9, 2013

(87) PCT Pub. No.: WO2012/139652
PCT Pub. Date: Oct. 18, 2012

(65) Prior Publication Data
US 2014/0024859 A1   Jan. 23, 2014

(51) Int. Cl.
| | | |
|---|---|---|
| *C07C 209/48* | (2006.01) |
| *B01J 8/22* | (2006.01) |
| *B01J 19/00* | (2006.01) |
| *B01J 38/72* | (2006.01) |
| *B01J 25/02* | (2006.01) |
| *B01J 25/04* | (2006.01) |
| *B01J 38/48* | (2006.01) |

(52) U.S. Cl.
CPC .............. *C07C 209/48* (2013.01); *B01J 8/226* (2013.01); *B01J 8/228* (2013.01); *B01J 19/0053* (2013.01); *B01J 38/72* (2013.01); *B01J 25/02* (2013.01); *B01J 25/04* (2013.01); *B01J 2219/00006* (2013.01); *B01J 38/48* (2013.01)
USPC .......................................................... 564/492

(58) Field of Classification Search
USPC .......................................................... 564/492
See application file for complete search history.

(56) References Cited

U.S. PATENT DOCUMENTS

| | | | |
|---|---|---|---|
| 4,395,573 A * | 7/1983 | Cutchens et al. | 564/492 |
| 4,429,159 A | 1/1984 | Cutchens et al. | |
| 6,232,488 B1 * | 5/2001 | Boschat et al. | 558/459 |
| 2010/0267989 A1 * | 10/2010 | Letourneur et al. | 564/511 |

OTHER PUBLICATIONS

Search report from PCT/EP2011/055996; 3 pgs, (mailed Apr. 11, 2011).

* cited by examiner

*Primary Examiner* — Brian J Davis
(74) *Attorney, Agent, or Firm* — Gifford, Krass, Sprinkle, Anderson & Citkowski, P.C.

(57) ABSTRACT

It is described a process for the production of hexamethylenediamine by hydrogenation of adiponitrile, comprising an improved step of regeneration of the catalyst. Also described are an equipment for the production of hexamethylenediamine, and a washing apparatus (14) for implementing the catalyst regeneration step.

16 Claims, 2 Drawing Sheets

PROCESS FOR THE PRODUCTION OF HEXAMETHLENEDIAMINE

CROSS-REFERENCE TO RELATED APPLICATIONS

This application is the U.S. National Phase of PCT/EP2011/055996 filed Apr. 15, 2011.

FIELD OF THE INVENTION

The present invention relates to an improved process for the production of hexamethylenediamine by catalytic hydrogenation of adiponitrile; in particular, the invention is about a process comprising the continuous regeneration of the catalyst.

BACKGROUND ART

Hexamethylenediamine, also abbreviated HMD in the rest of the description, to is an important chemical for industrial applications. The great part of the world production of this substance is used for manufacturing nylon 6-6 via condensation with adipic acid, with minor amounts used in the production of polyurethanes or as cross-linking agent in epoxy resins.

The present process for the production of HMD is essentially based on the teachings of U.S. Pat. No. 3,821,305, entirely incorporated herein by reference. Briefly, in the process described in said patent, adiponitrile (also abbreviated ADN in the rest of the description) and hydrogen are simultaneously fed to the bottom of a reaction column, filled with HMD produced in the reaction, a caustic alkali, water and a Raney-type catalyst (e.g., Raney Nickel). Concentration ratios of the species present in the reactor must be kept in given ranges, in order to ensure the total conversion of ADN with a good yield to HMD, and very low amounts of impurities; also important for assuring good results are the continuous agitation of the reacting system, a hydrogen partial pressure kept constantly in the range of 10 to 50 bar (gauge pressure), and a temperature maintained in the range from 60 to 100° C.

Under these conditions, the reaction medium is essentially a liquid mixture HMD-water, containing between 93% and 97% by weight of HMD, in which the particles of the metallic catalyst are suspended; the caustic alkali (preferably caustic soda, NaOH) is essentially insoluble in the HMD-water mixture and gives rise to a separated liquid phase, a water solution of concentration between about 25% to 55% by weight of the alkali, that is present in the reacting system in the form of a film on the surface of the catalyst particles.

A known problem with this type of process is the high rate of deactivation of the catalyst, which leads to a reduced overall rate of ADN conversion and a reduced selectivity towards HMD, thus leading to an increase in the production of impurities.

A first possible cause of deactivation is the settling of the catalyst, which is heavier than the HMD-water mixture, in dead-ends of the reactor vessel; the catalyst that settles in certain points of the vessel does not take part anymore in the reaction and undergoes rapid deactivation, and must be replaced with fresh catalyst.

Another main factor in the catalyst deactivation is the build-up of nitrile groups of ADN on the catalyst surface. The paper "Hydrogenation of adiponitrile catalyzed by Raney Nickel. Use of intrinsic kinetics to measure gas-liquid mass transfer in a gas induced stirred slurry reactor", C. Mathieu et al, Chemical Engineering Science vol. 47 no 9-11, 2289-94 (1992), describes that Raney-type catalysts such as nickel or cobalt, when used in low-pressure hydrogenation processes as in the present case, are rapidly deactivated by the accumulation of non-reacted nitrile groups at the liquid-solid interface between the reaction medium and the catalyst. Said accumulation can be favoured by a non-uniform dispersion of ADN in the reacting mixture, that can give rise to zones of the mixture where a high concentration of this chemical is present.

According to U.S. Pat. No. 3,821,305 it is necessary to adopt measures for keeping the catalyst activity above a minimum value. The effectiveness of the "hydrogenating capability" of the catalyst bulk on the reaction can be expressed as a function of the concentration of the suspended catalyst (e.g., by weight) in the reaction medium together with its average residual potential activity in terms of amount of hydrogen contained in the catalyst, measured e.g. in normal $cm^3$ of $H_2$ per gram of catalyst, $Ncm^3_{H2}/g_{CAT}$; typical values of activity of the fresh catalyst are comprised between about 60 and 80 $Ncm^3_{H2}/g_{CAT}$. In practice, only part of this potential capability can be used for the reaction, due to phenomena occurring in the course of the running time, like the catalyst particle size mechanical fragmentation, increasing the fines content of the catalyst's mass, or the catalyst particles poisoning, leading to a statistical distribution of activities in the catalyst bulk, according to different levels of deactivation of the catalyst particles.

A good operation of the hydrogenation on a steady state condition must take care of these phenomena, introducing the operations helpful to maintain the "hydrogenation capability" of the catalyst bulk constant during the operation and well related to the desired production rate.

The paper "Gas holdup and liquid recirculation in gas-lift reactors", Y. C. Hsu et al., Chemical Engineering Science, Vol. 35, 135-141 (1980) teaches that the presence of zones of the reacting mixture of high ADN concentration can be avoided by adopting conditions that create turbulent flow in the reaction medium; this can be obtained for instance through high liquid recirculation speeds in the reactor. The same problem is tackled by U.S. Pat. No. 6,281,388 B1, that discloses the use of mixers, preferably a static mixer, to enhance the dispersion in the reaction mixture of the ADN fed to the same. Finally, Patent application US 2010/0130789 A1 describes a HMD production process taking place in a plug-flow reactor, in which the catalyst is maintained at the desired activity level through the control of the feeding rate into the reactor of the nitrile and/or the catalyst, in such a way as to keep in a desired range the ratio of moles of nitrile fed per unit time to flow rate by weight of catalyst.

The adoption of these measures, however, can only reduce but not avoid the deactivation of the catalyst, that must thus be continuously refreshed to maintain the efficiency of the reaction at suitable levels for industrial applications. Refreshing of the catalyst is generally obtained in known processes by extracting a portion of the reacting mixture from the reactor; separating the catalyst from the liquid phase, which is sent to purification processes downstream the reaction for the recover of HMD; subjecting the spent (or partially spent) catalyst to a regeneration treatment; and feeding back the regenerated catalyst to the reaction. In practice, in order to improve the average activity of the catalyst, generally only part of regenerated catalyst is fed back into the reactor, the remainder part being discharged; the amount of discharged catalyst is replaced by an equal quantity of fresh catalyst.

The regeneration of the spent (or partially spent) catalyst is aimed to remove organic compounds (generally polyamines)

and inorganic compounds (generally alumina and aluminates) formed in the hydrogenation process, that could clog the pores of the catalyst, hindering the transport of hydrogen to the inner surfaces of the pores and thus inhibiting, and in the end quenching, the catalyst activity.

The regeneration of Raney catalysts is the subject of some patent documents.

U.S. Pat. No. 6,518,449 B1 discloses a process for the hydrogenation of nitriles with a Raney catalyst in which the spent catalyst, separated from the reaction mixture, is treated with an aqueous alkali solution, in which the anion concentration is at least 0.01 mol/l, at a temperature below 130° C.; the catalyst is then washed with water or an alkali solution, until the pH of the washing water is in the range between 12 and 13.

Patent application US 2010/0267989 A1 describes a HMD production process taking place in a plug-flow reactor, in which a portion of the reacting mixture is continuously withdrawn at the outlet of the reactor and the catalyst contained in said portion is separated from the liquid phase and sent to a regeneration stage, consisting in a first operation of washing with water to remove most of the organic compounds, then a treatment with an inorganic base in order to remove aluminates, and finally a washing step with water or a alkali metal hydroxide solution.

The methods described in these documents suffer however from the drawback of requiring the use of relatively high volumes of basic solutions needing to be disposed of in a safe manner, which generally involves lengthy and energy-intensive pre-conditioning treatments.

SUMMARY OF THE INVENTION

It is an object of the present invention to provide an improved process for the production of hexamethylenediamine by catalytic hydrogenation of adiponitrile, comprising a continuous regeneration of the catalyst that solves the problems of the prior art.

It is another object of the invention to provide an apparatus that realizes said continuous regeneration.

These objects are achieved with the present invention which in a first aspect concerns a process for the production of hexamethylenediamine by hydrogenation of adiponitrile, comprising: feeding hydrogen and adiponitrile into a reactor containing a Raney catalyst, water and inorganic base to form a reaction medium; mixing the reaction medium to provide a uniform concentration of adiponitrile in the reactor; and hydrogenating adiponitrile to form hexamethylenediamine; said process characterized in that:
  a flow of reaction medium comprising the catalyst is continuously extracted from the reactor and sent to a washing apparatus, said flow crossing said apparatus in a given direction;
  water is continuously fed to the washing apparatus, and caused to cross it in counter-flow with respect to said flow of reaction medium;
  a water-rich solution containing hexamethylenediamine and the inorganic base, resulting from the washing of the catalyst, is continuously sent to a first tank;
  raw hexamethylenediamine extracted from the hydrogenation reactor is continuously fed to said first tank and mixed with said water-rich solution, so as to obtain an overall mixture composition such that phase separation takes place between a first phase consisting in a water based solution containing essentially all of the inorganic base and a second phase being consisting in a water-hexamethylenediamine solution;
  a suspension in water of the washed catalyst is continuously extracted from the washing apparatus, sent to a sedimentation tank, and after separation of water, a part of the regenerated catalyst is fed back to the hydrogenation reactor, the part not fed back to the reactor being compensated by the addition of fresh catalyst.

The process of the present invention has several characterizing features. In first place, washing of the catalyst is carried out with simple water, rather than with the basic solutions required by prior art processes; this reduces the overall amount of potentially dangerous chemicals involved in the process. In second place, the alkaline solution derived from the washing of the catalyst is extracted in the form of a concentrated solution of HMD containing all of the inorganic base, thus of relatively low volume when compared to prior art methods, which makes possible and easier the subsequent treatments the solution must undergo. Other advantages, that will be apparent from the following detailed description, comprise the fact that the continuous washing of the catalyst of the present invention allows an optimized consumption of the water used for the operation, while affording an effective recovery of HMD. This optimization makes feasible to shorten processing times and recirculation rate of the catalyst, thus affording a reduction of the total amount of catalyst involved in HMD manufacturing process, and reducing the risks in operation and the working capital costs. Furthermore, the improved effectiveness of inorganic base separation also minimizes the dangerous effects, well-known in the field, connected to stress corrosion cracking caused by alkali at high temperature that could take place in particular in the purification section of the plant, especially in hot dead zones that are commonly present in plant equipment, e.g. those employed in distillation operations.

DETAILED DESCRIPTION OF THE INVENTION

The process of the invention is characterized, among other features, by the continuous extraction of part of the reaction medium, to be sent to the catalyst regeneration stage, continuous regeneration of the catalyst and continuous feed-back of the same to the hydrogenation reactor. The process is described below with reference to FIGS. 1 and 2. In the description that follows, all percentages are by weight (b.w.) unless different units are specified. In the description that follows, reference will often be made to caustic soda, NaOH, that is the preferred inorganic base, but it is understood that other inorganic bases, such as KOH, can be used in the invention as well.

Figure 1:
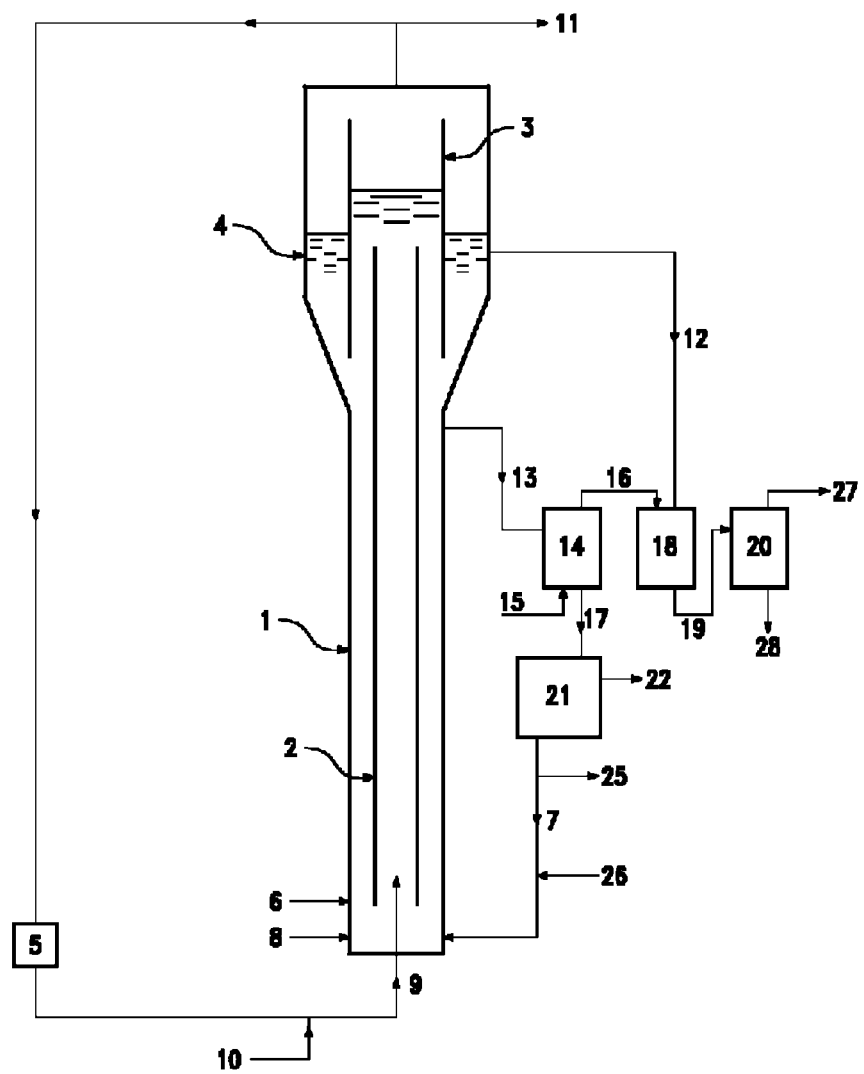
FIG. 1 is a schematic illustration of the complete equipment for HMD production that realizes the process of the invention.

FIG. 1 shows the complete equipment for the production of HMD (the subsequent stages for HMD purification are not shown). The hydrogenation reactor is of the "gas lift" type, namely, such that a reactant gas is fed to the bottom of the reactor and allowed to diffuse in the reaction medium, also causing natural agitation of the same. This reactor, and the process carried out within it, are essentially similar to the ones described in U.S. Pat. No. 3,821,305.

Briefly, the reactor is in the form of a vertical tubular reaction vessel, 1, provided inside with an ejection device, 2, such as to promote the agitation of the reaction medium resulting from the hydrogen flow, and at the top with other devices, 3 and 4, which enable the separation of the gas from the liquid and the drawing off from the reaction vessel of the hydrogenated product, having a low content of catalyst, thus making it possible to maintain in the reaction vessel relatively high concentrations of catalyst.

The top of the reactor is connected, through a gas pipe, to a gas re-cycling pump, 5, for feeding back hydrogen to the bottom of the reactor. To the bottom of the reactor are also connected pipes for feeding the reaction vessel with adiponitrile, 6, aqueous suspension of catalyst, 7, aqueous solution of caustic soda, 8, and hydrogen, 9. The hydrogen consumed in the reaction is replaced by feeding fresh hydrogen through pipe 10.

Part of the gas is vented through pipe 11, the purpose of this release being to maintain the hydrogen content in the recycled gas above a given value.

The output of clarified hexamethylenediamine is discharged through pipe 12.

Pipe 13 is used for removing an amount of reaction medium whose catalyst content is equivalent to the amount supplied through pipe 7. In this way, the concentration of catalyst in the reaction medium remains constant.

The main process parameters are: a reaction temperature comprised between 60 and 100° C., and preferably between 70 and 90° C.; a hydrogen partial pressure comprised between 10 and 50 bar, preferably between 20 and 35 bar, over atmospheric pressure; a $H_2O/NaOH$ molar ratio in the reaction medium comprised between 2 and 130, preferably between 7 and 70; a NaOH/catalyst ratio in the reaction medium comprised between 0.2 and 12 (preferably between 0.3 and 3) moles of NaOH per kg of catalyst; and a catalyst concentration in the reaction medium comprised between 1 and 35%, preferably between 10 and 30% b.w. It has been observed that operating in these ranges allows to maximize both the rate of conversion of ADN and the selectivity of the reaction towards HMD (namely, the formation of by-products is kept as low as possible).

Further to what is described in U.S. Pat. No. 3,821,305, the equipment of the present invention comprises a washing apparatus, 14, that continuously receives, in a top part of it, a flow of reaction medium from pipe 13, and in a bottom part thereof a flow of water from pipe 15; the water fed through line 15 is preferably demineralized water. In apparatus 14 takes place the washing of the catalyst from the organic and inorganic compounds.

The catalyst enters the apparatus from the upper part of it and moves downward due to gravity; water enters the apparatus from the bottom of the same and moves upwards due to the push exerted by a water feeding pump (or any other means, such as a water reservoir placed higher, and thus having higher hydrostatic pressure, than apparatus 14; said pump or means are not shown in the drawing).

During its upward movement, water removes organic and inorganic compounds referred to before from the catalyst surface. The liquid phase leaving apparatus 14 from its upper part is a water-rich HMD solution, containing the inorganic base transported in the washing apparatus by the catalyst and said organic and inorganic compounds; this liquid phase is fed, through pipe 16, to a first tank, 18. To tank 18 is also continuously fed, through line 12, a flow of raw HMD produced in the reactor. Tank 18 is preferably agitated, so as to favour homogenization of the liquid mixture therein. The flow incoming from line 12 is set to a rate such that, combined with the flow of liquid phase coming from pipe 16, gives rise in tank 18 to a HMD-rich mixture of overall composition such to be instable; the HMD content of this mixture must be at least 75%, and preferably at least 88%. From the bottom of this tank 18, this mixture is fed to tank 20, through line 19. As known in fact in the field, in alkali-water-HMD systems, when water is present at concentrations below about 30%, the system is not stable and separates into a HMD-water solution and a water-based phase, immiscible in the former one, containing a major part of the alkali originally present. The alkali-containing water solution produced in tank 20 is sent to disposal through line 28.

An important result of said separation is that the HMD-containing phase that leaves tank 20 has a content of alkali compounds significantly lower than in prior art methods; the inventors have observed that this spontaneous separation allows the removal of up to 80% of the alkali coming from catalyst regeneration, that otherwise would enter the HMD purification stage. The thus obtained HMD-water solution, extracted from tank 20 via line 27, can thus be sent to purification stages for the recovery of HMD, without the need of a previous dedicated alkali removal treatment. The inventors have found that operating this way, the overall HMD recovery from the process is better than 98% of the amount sent to the washing apparatus together with the catalyst. Operating otherwise, according to prior art methods, this result cannot be reached, and the maximum possible HMD recovery comes from a compromise with the need of carrying out an efficient separation of the alkali upstream the purification stage.

The catalyst fed to the top of washing apparatus 14 reaches the bottom of the same cleaned from impurities and thus regenerated, and leaves the washing apparatus via pipe 17 in the form of a water suspension, reaching a sedimentation tank, 21; in this tank, the catalyst settles due to gravity, giving rise to supernatant, essentially catalyst-free water, that is extracted from the system via pipe 22, and a humid catalyst mass that is fed back to the reactor via line 7. Lines 25 and 26 are respectively used to draw some "spent" catalyst from the reactor and to add some fresh catalyst in order to keep reaction efficiency at a desired level as previously stated.

Figure 2:
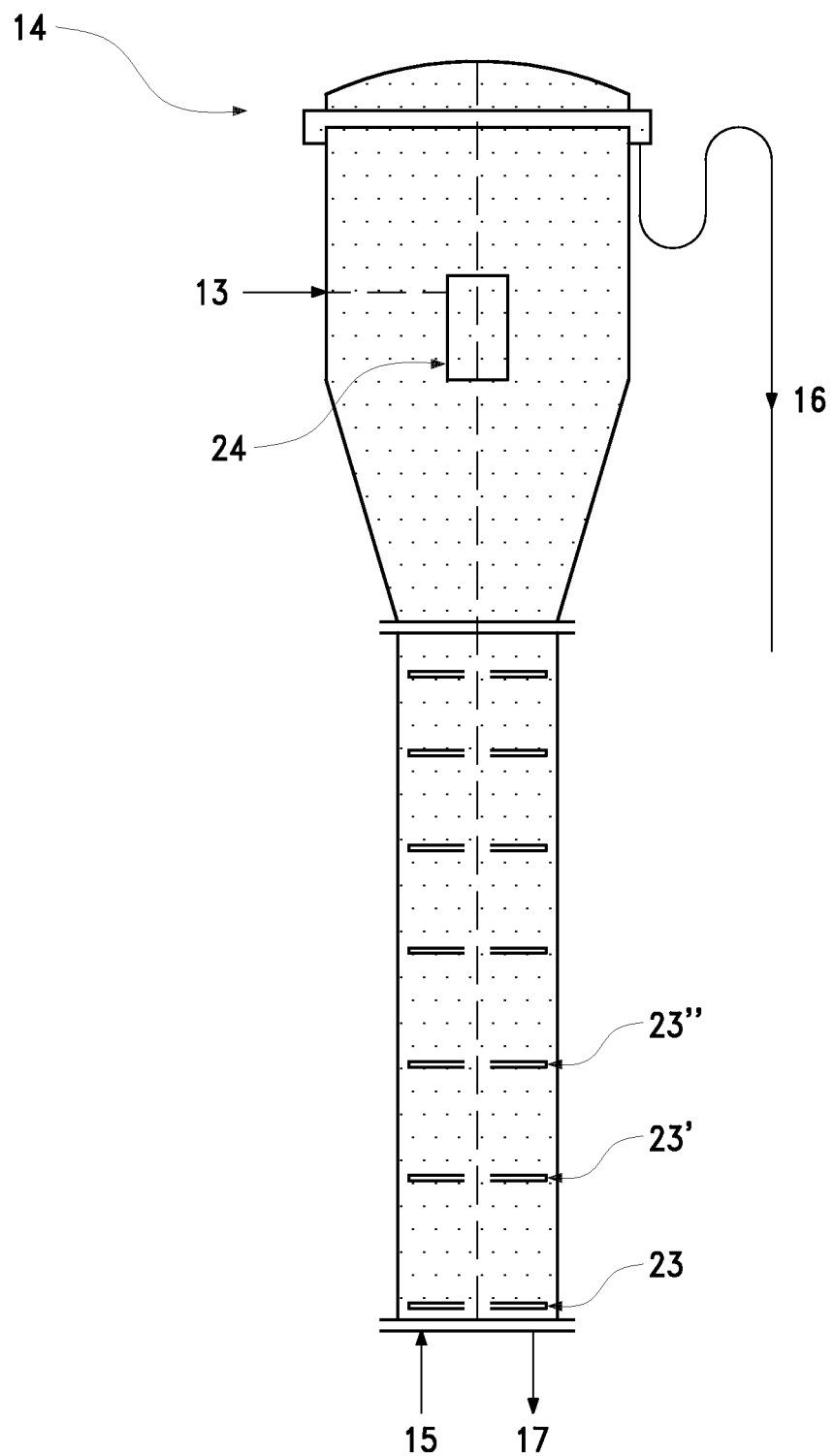
FIG. 2 is a schematic illustration, in cross section, of a preferred washing apparatus for use in the process of the invention.

The washing apparatus, 14, has preferably a tower structure as shown schematically in FIG. 2. The tower contains several trays 23, 23', 23", . . . , at different levels, not necessarily equi-spaced along the axis of apparatus 14, and is connected to pipes 13, 15, 16 and 17, as explained above. The number of trays is conveniently comprised between 2 and 100, and preferably between 5 and 40. The trays divide the inner space of the tower in a number of volumes, each one corresponding to a washing stage in the washing operation. Each tray presents openings, such as to allow the falling of the catalyst from one tray to the one immediately below; to this end, the openings in next trays, when seen in a top view, are not corresponding, and any pair of next trays would be seen as "blind" in such top view. The overall area of openings in each tray is comprised between about 1 and 50%, and preferably between 5 and 25%, of the area of the tray itself.

The reaching of the openings of the catalyst, and thus the passage of the same from a washing stage to the next (that is, from one tray to the one immediately below) may be caused by natural agitation induced in the system by liquids flow; preferably, however, the phenomenon is favored by mechanical means, for instance a series of blades, one per each tray, connected to a central rotating shaft (blades and shaft not shown in FIG. 2), that "sweep" the trays surface moving the catalyst deposited thereon towards the openings.

The dimensions of the tower, the number of washing stages, and if present, the rotational speed of the sweeping blades, control the residence time of the catalyst in the tower and thus the washing effectiveness of the washing operation.

In the upper part of apparatus 14, where the flow of reaction medium from pipe 13 is received, is optionally present a sedimentation zone, 24, where the catalyst is allowed to settle before being sent to the washing stages. This zone has the function of enhancing as much as possible the settling of catalyst fines, thus reducing their carry-over with the HMD-water solution leaving the washing apparatus from its upper part. In practice, this zone may be produced by inserting, e.g., a bundle of tubes or a cyclon in the upper part of apparatus 14 (the part receiving the flow from pipe 13), in such a way to slow down in this zone the ascending speed of liquids flow thus minimizing the turbulence and decreasing the kinetic energy of solid particles to minimize the carry-over of the finest catalyst particles.

The operating parameters of the washing tower may be adjusted to achieve an optimal washing effectiveness with minimum water consumption.

The aim of catalyst washing is to bring back its activity in a range comprised between about 40 and 70% of its original activity. The inventors have observed that, in order to achieve this result, it is necessary to run the continuous washing treatment in such a way to satisfy at the same time several conditions. In first place, it must be assured that the water suspension of the catalyst leaving the bottom of the tower has a residual alkalinity degree, expressed as HMD percent b.w., lower than 1%, and better lower than 0.5%. Second, the best washing performances are obtained by controlling the composition of the solution leaving the top part of the washing tower, in such a way that this solution has a content of HMD of at least 20% and preferably of at least 45% b.w. Then, it is important to control the concentration of the catalyst in the water suspension leaving the bottom of the tower, so that this is below 25%, and preferably between 5 and 15% b.w. Finally, the washing treatment must be followed by post-treatments assuring a proper water content in the hydrogenation reactor, comprised between 1 and 10%, and preferably between 3 and 6% b.w. of the liquid phase; this can obtained by controlling the residence time of the catalyst suspension in sedimentation tank 21.

The actual values of the above-cited parameters cannot be given precisely, because these depend on the dimensions of the hydrogenation reactor and of the washing apparatus, on constructive details of the same, on the production and catalyst regeneration rates imposed to the overall system, or finally, on the particle size distribution of the catalyst; however, for any given assembly reactor/washing apparatus and actual catalyst, the run parameters that allow to satisfy the conditions above can be easily determined with a few trials.

The inventors have found that the amount of water necessary for washing the catalyst is comprised between 0.1 and 10 kg, and preferably between 0.5 and 3 kg, per 1 kg of reaction medium fed to apparatus 14 through pipe 13. This actual value of the ratio also includes the amount of water necessary to keep the washed catalyst suspension fluid enough for it to be moved across the system, and that can optionally be added in a separated container downstream the washing apparatus (that is, not all the water necessary to satisfy the above ratios needs to be fed to the bottom of the washing apparatus).

For the washing action to be effective, it is necessary to send to the washing step an amount of catalyst lower than 0.5 kg, preferably between 0.001 and 0.05 kg, per kg of ADN fed to the reactor. As stated above, there is the need of replacing part of the employed catalyst with fresh catalyst; the inventors have found that the best results are achieved using between 0.3 and 2 kg, preferably between 0.4 and 0.9 kg, of fresh catalyst per 1,000 kg of HMD produced.

The invention will be further illustrated by the following examples.

EXAMPLE 1

A continuous process of hydrogenation of ADN to HMD is carried out in a system of the kind described in the text with reference to FIGS. 1 and 2.

The reacting mixture in reactor 1 comprises a liquid phase of HMD and by-products (about 95% b.w.), water (about 4% b.w.), NaOH (0.6% b.w.), and a solid suspension of Chromium-containing Raney Nickel catalyst (20% b.w. of the total amount of the reacting mixture); this mixture is kept agitated by a continuous flow of recirculating hydrogen at a temperature of 80° C. and under a partial pressure of hydrogen of 29 bar over ambient pressure (gauge pressure). Under these conditions a continuous flow of ADN is fed through line 6 to the reactor, together with a suspension of catalyst and a solution of NaOH at 30%. Fresh hydrogen is fed to the reactor through the line 10 to compensate the hydrogen reacted and to keep the pressure constant.

Simultaneously, a flow of the reacted mixture, almost free of catalyst particles separated in devices 3 and 4, is extracted via line 12 and sent to tank 18. Through line 13, a second part of the reacted mixture is continuously extracted from the reactor and fed to a washing apparatus (14) like the one shown in FIG. 2; this apparatus is 9.1 m high, and comprises 25 trays each one having a surface of the openings equal to 14% of the surface of the tray; a rotating axle coaxial with the washing apparatus, passing through a central aperture of each tray, carries 25 blades in positions corresponding to the upper surface of each tray, to move the catalyst that settles on the trays toward the openings thus favoring the overall downward movement of the catalyst in the apparatus.

Deionised water is continuously fed in the bottom part of apparatus 14 through line 15. The result of this washing process is the extraction, from the top of the apparatus (line 16) of a water-based solution containing 55% b.w. of amine compounds, and from the bottom (line 17) a water suspension containing 13% b.w. of catalyst. This way, a concentration of amine compounds in the catalyst recirculation waters lower than 0.2% b.w. is obtained, while the regenerated catalyst has an activity, measured as $Ncm^3_{H2}/g_{CAT}$, equal to about 65% of the activity of the fresh catalyst. To achieve this result of activity regeneration, the catalyst is washed at a rate of 1 kg of catalyst per 35 kg of ADN fed to the reactor and fresh catalyst consumption is 0.65 kg per 1,000 kg of HMD produced.

The water-based solution from line 16, containing all of the caustic soda present on the catalyst entering the washing apparatus, is fed to tank 18, to which is fed as well, through line 12, a flow of reacting mixture coming from the hydrogenation reactor. In tank 18 a HMD-rich mixture is thus formed, comprising amine compounds, water and NaOH. This mixture is unstable, and spontaneously separates into an organic phase and a water-based phase. In order to have an accurate analysis, which is not affected by external contributions (e.g. wall effect, vessel shape, residence time and so on), the mixture is centrifuged at 4000 rpm for 12 minutes. Afterwards, a sample of the organic phase is taken and analyzed to measure the sodium concentration with an inductive coupled plasma spectrometer, which results equal to 214 ppm expressed as NaOH. HMD concentration of this sample is as well analyzed by titration which results as well equal to 89.5% b.w referred to original sample mass.

EXAMPLE 2

The procedure of Example 1 is repeated up to step in which the HMD-rich mixture in tank 18 is formed. To a sample of this mixture, water is added until the formation of a single phase, so to be able to analyze the whole soda amount of the sample before phase separation occurs. A sample of this single phase solution is taken and its sodium concentration is measured which, taking into account water dilution, results equal to 901 ppm expressed as NaOH. This means that about 76% of sodium of the original mixture can be separated in tank 18. From these data, the overall composition of the fluid resulting from mixing of line 12 with line 16 can be calculated, that is: HMD 89.5%, as stated in Example 1, NaOH 901 ppm and, by difference, water approx. 10.4%. These data are reported as example 1 in Table 1 and as Example 1-2 in Table 2.

EXAMPLES 3-12 (COMPARATIVE)

A series of washing tests are carried out in discontinuous conditions, as known in the field.

A continuous process of hydrogenation of ADN to HMD is carried out as described in Example 1. A part of the reacting mixture is extracted from the reactor and placed in a separate tank; the mixture is first agitated, then agitation is discontinued allowing the catalyst to settle, and the supernatant liquid is removed. Water is then added to the catalyst wet cake in such an amount that the concentration of amines in the water suspension is lower than 0.5% b.w. The addition of water is carried according to different addition schedules; in particular, in a first experiment (test 3) all of the water necessary to produce a suspension with amines concentration lower than 0.5% b.w. is added in a single step; the other tests (4-12) are carried out by subdividing the overall amount of water in several subsequent additions followed by agitation, settling of the catalyst, and removal of the liquid before the next addition, until the target amines concentration is obtained. Another condition checked in the tests is the n-th number of washing step whose waters need to be collected to recover at least 99.5% of the HMD initially placed in the tank.

Parameters and results of this test are summarized in Table 1, that reports:
 the Example whose conditions are summarized (heading "Example" in the table);
 the number of water addition steps ("Water additions");
 the number of n-th washing step after which 99.5% of HMD is recovered ("Recovered washings");
 the overall composition of a given test, in % b.w., resulting from the sum of all water additions in that test ("Overall composition");
 the amount of recovered HMD, as % over the HMD initially placed in the tank ("HMD recovered");
 the weight ratio between water used and recovered HMD in the given test ("H₂O/HMD ratio").

EXAMPLE 13 (COMPARATIVE)

In order to evaluate maximum soda separation yield, as done in Example 1, two mixtures, with composition as of those of examples 7 and 12, are prepared. The organic phases are then analyzed with the same technique described in the examples above. Compositions of solutions prepared and soda found in organic phase after centrifugation are given in table 2. In table 2, it is not possible to give a value for separation value in example 7 since the difference between soda content before and after centrifugation is very low (5 ppm) and less than the mean error of the analytical method used. This means that in fact no phase separation occurs and so all the soda remains in the same phase of HMD and it is not possible to separate it as described before.

TABLE 2

| Composition | Original solution | | | After centrifugation | |
|---|---|---|---|---|---|
| | HMD (% b.w.) | $H_2O$ (% b.w.) | NaOH (ppm) | NaOH (ppm) | Separation yield |
| Examples 1-2 | 89.5 | 10.4 | 901 | 214 | 76% |
| Example 7 | 70.7 | 29.3 | 681 | 686 | NA |
| Example 12 | 77.2 | 22.7 | 750 | 694 | 7.5% |

Comments to the Results

The comparison between the data of concentration of sodium in the organic phase, resulting from the procedures of Example 1 and Example 2, shows that the process of the invention allows a noteworthy reduction in sodium content in the case of the invention. Similarly, the comparison in Table 2 of the same parameter from Example 1 and 2 with the results from Examples 7 and 12 shows that the process of the invention achieves a better yield in soda separation.

The comparison between conditions and results of the test of Example 1 on one side, and of Examples 3-12 on the other side (Table 1) shows first that, with discontinuous washings, in order to obtain figures of HMD recovery higher than 99.5% it is necessary use more or much more water than it is necessary with the process of the invention; this implies a greater degree of soda retention in the washing waters, and a greater consumption of energy for water evaporation when it comes to HMD separation. The further advantage is obtained of avoiding caustic stress corrosion cracking linked to localized setting of concentrated soda solutions.

Other useful results or advantages over the prior art methods achieved by the present invention are that the process is simple, employing in the washing steps only demineralized

TABLE 1

| Example | Water additions | Recovered washings | Overall composition (% b.w.) | | | HMD recovery | $H_2O$/HMD ratio |
|---|---|---|---|---|---|---|---|
| | | | HMD | $H_2O$ | NaOH | | |
| 1 | Continuous | N/A | 89.5 | 10.4 | 0.09 | 99.65 | 0.12 |
| 3 | 1 | 1 | 3.85 | 96.15 | 0.004 | 99.88 | 25.00 |
| 4 | 2 | 2 | 31.39 | 68.58 | 0.03 | 99.88 | 2.18 |
| 5 | 3 | 3 | 48.35 | 51.61 | 0.05 | 99.88 | 1.07 |
| 6 | 4 | 4 | 56.63 | 43.32 | 0.05 | 99.88 | 0.77 |
| 7 | 5 | 4 | 70.74 | 29.20 | 0.07 | 99.58 | 0.41 |
| 8 | 6 | 5 | 71.65 | 28.28 | 0.07 | 99.66 | 0.39 |
| 9 | 7 | 6 | 72.30 | 27.64 | 0.07 | 99.70 | 0.38 |
| 10 | 8 | 7 | 72.77 | 27.16 | 0.07 | 99.73 | 0.37 |
| 11 | 9 | 7 | 77.69 | 22.23 | 0.07 | 99.52 | 0.29 |
| 12 | 10 | 8 | 77.45 | 22.47 | 0.07 | 99.58 | 0.29 | water in contrast with some prior art methods that use basic solutions; the amount of catalyst involved in the washing steps is reduced, which reduces the dangers linked to its handling (the catalyst is pyrophoric); and, the HMD concentration of the solution coming from the washing operation is less to variable than in case of discontinuous washing processes, that makes easier the separation of soda.

The invention claimed is:

1. A process for the production of hexamethylenediamine by hydrogenation of adiponitrile, comprising: feeding hydrogen and adiponitrile into a reactor comprising a Raney catalyst, water and inorganic base to form a reaction medium; mixing the reaction medium to provide a uniform concentration of adiponitrile in the reactor; and hydrogenating adiponitrile to form hexamethylenediamine;

said process characterized in that:
a flow of reaction medium comprising the catalyst is continuously extracted from the reactor and sent to a washing apparatus, said flow crossing said apparatus in a given direction;
water is continuously fed to the washing apparatus, and caused to cross it in counterflow with respect to said flow of reaction medium;
a water-rich solution containing hexamethylenediamine and the inorganic base, resulting from the washing of the catalyst, is continuously sent to a first tank;
raw hexamethylenediamine extracted from the hydrogenation reactor is continuously fed to said first tank and mixed with said water-rich solution, so as to obtain an overall mixture composition such that phase separation takes place, in a second tank, between a first phase consisting in a water based solution containing essentially all of the inorganic base and a second phase consisting in a water-hexamethylenediamine solution;
a suspension in water of the washed catalyst is continuously extracted from the washing apparatus, sent to a sedimentation tank, and after separation of water, a part of the regenerated catalyst is fed back to the hydrogenation reactor, the part not fed back to the reactor being compensated by the addition of fresh catalyst.

2. The process according to claim 1, wherein the production of hexamethylenediamine by hydrogenation of adiponitrile takes place at a temperature comprised between 60 and 100° C., a hydrogen partial pressure comprised between 10 and 50 bar over atmospheric pressure, a water/inorganic base molar ratio in the reaction medium comprised between 2 and 130, a inorganic base/catalyst ratio in the reaction medium comprised between 0.2 and 12 moles of inorganic base per kg of catalyst, and a catalyst concentration in the reaction medium comprised between 1 and 35% b.w.

3. The process according to claim 1, in which raw hexamethylenediamine extracted from the hydrogenation reactor is mixed with said water-rich solution in said first tank in a flow-rates ratio such that the resulting hexamethylenediamine-rich mixture contains at least 75% b.w. of hexamethylenediamine.

4. The process according to claim 3, in which said hexamethylenediamine content is at least 88% b.w.

5. The process according to claim 1, in which said suspension in water of the washed catalyst has a catalyst concentration lower than 25% b.w.

6. The process according to claim 5, wherein the catalyst concentration in said suspension is comprised between 5 and 15% b.w.

7. The process according to claim 1, in which said suspension in water of the washed catalyst has a hexamethylenediamine content lower than 1% b.w.

8. The process according to claim 7, in which the hexamethylenediamine content of said suspension is lower than 0.5% b.w.

9. The process according to claim 1, in which said water-rich solution containing hexamethylenediamine and the inorganic base, continuously sent to said first tank, has a hexamethylenediamine content of at least 20% b.w.

10. The process according to claim 9, in which the hexamethylenediamine content of said water-rich solution is at least 45% b.w.

11. The process according to claim 1, in which the ratio water/reaction medium continuously fed to said washing apparatus is comprised between 0.1 and 10 b.w.

12. The process according to claim 11, in which said ratio is comprised between 0.5 and 3 b.w.

13. The process according to claim 1, in which the catalyst is sent to the washing step in an amount lower than 0.5 kg per kg of adiponitrile fed to the hydrogenation reactor.

14. The process according to claim 11, in which the catalyst is sent to the washing step in an amount comprised between 0.001 and 0.05 kg per kg of adiponitrile fed to the hydrogenation reactor.

15. The process according to claim 1, in which fresh catalyst is fed to the hydrogenation reactor in an amount comprised between 0.3 and 2 kg per 1,000 kg of hexamethylenediamine produced.

16. The process according to claim 15, in which fresh catalyst is fed to the hydrogenation reactor in an amount comprised between 0.4 and 0.9 kg per 1,000 kg of hexamethylenediamine produced.

* * * * *